United States Patent
Elliott et al.

(10) Patent No.: US 11,517,265 B1
(45) Date of Patent: Dec. 6, 2022

(54) PERSONAL HAND-HELD MONITOR TO PRODUCE A THEORETICAL CURVE BASED ON PPG SIGNALS AT DIASTOLE AND SYSTOLE, MEASURED PRESSURE DATA AT DIASTOLE AND SYSTOLE, AND TIMES OF DIASTOLE AND SYSTOLE

(71) Applicant: LEMAN MICRO DEVICES SA, Lausanne (CH)

(72) Inventors: Christopher Elliott, St Sulpice (CH); Mark-Eric Jones, Penthalaz (CH); Shady Gawad, Lonay (CH); Sebastien Emonet, Trelex (CH); Didier Clerc, Monthey (CH)

(73) Assignee: Leman Micro Devices SA, Lausanne (CH)

( * ) Notice: Subject to any disclaimer, the term of this patent is extended or adjusted under 35 U.S.C. 154(b) by 989 days.

(21) Appl. No.: 15/999,844

(22) PCT Filed: Feb. 15, 2017

(86) PCT No.: PCT/EP2017/053441
§ 371 (c)(1),
(2) Date: Aug. 20, 2018

(87) PCT Pub. No.: WO2017/140748
PCT Pub. Date: Aug. 24, 2017

(30) Foreign Application Priority Data

Feb. 18, 2016 (GB) .................................... 1602875

(51) Int. Cl.
*A61B 5/00* (2006.01)
*A61B 5/021* (2006.01)
*A61B 5/024* (2006.01)

(52) U.S. Cl.
CPC ............ *A61B 5/6898* (2013.01); *A61B 5/021* (2013.01); *A61B 5/7278* (2013.01); *A61B 5/02427* (2013.01); *A61B 2562/0247* (2013.01)

(58) Field of Classification Search
CPC ..... A61B 5/6898; A61B 5/7278; A61B 5/021; A61B 5/02427; A61B 2562/0247
See application file for complete search history.

(56) References Cited

U.S. PATENT DOCUMENTS

| 4,440,716 A | 4/1984 | Smith |
| 2014/0024905 A1 | 1/2014 | Sarrafzadeh et al. |

(Continued)

FOREIGN PATENT DOCUMENTS

| CN | 103327894 A | 9/2013 |
| CN | 105095635 A | 11/2015 |

(Continued)

OTHER PUBLICATIONS

Arquivos Brasileiros de Cardiologia Journal, Sociedade Brasileira de Cardiologia MCMXLIII; vol. 85, Suppl. 2, Jul. 2005; 25 pages.

(Continued)

*Primary Examiner* — Christopher Koharski
*Assistant Examiner* — Richmond J Van Winter
(74) *Attorney, Agent, or Firm* — BakerHostetler

(57) ABSTRACT

The present application describes a Personal Hand-Held Monitor (PHHM) of the type described in WO 2013/002165, WO 2014/125431, and International Patent Application No. PCT/EP2015/079888, with improved aspects to find indicators of health, and other improvements that facilitate its construction and calibration.

11 Claims, 10 Drawing Sheets

(56) References Cited

U.S. PATENT DOCUMENTS

2015/0031965 A1* 1/2015 Visvanathan ........ A61B 5/0205
600/301
2015/0374249 A1* 12/2015 Elliott .................... A61B 5/742
600/301

FOREIGN PATENT DOCUMENTS

| WO | WO 2013/001265 | 1/2013 |
| --- | --- | --- |
| WO | WO 2014/125431 | 8/2014 |
| WO | 2015184029 A1 | 12/2015 |
| WO | WO 2016/096919 | 6/2016 |

OTHER PUBLICATIONS

Lowess Smoothing in Statistics: What is it? http://www.statisticshowto.com/lowesssmoothing/; Accessed on Dec. 14, 2018; 5 Pages.

Painter "The velocity of the arterial pulse wave: a viscous-fluid shock wave in an elastic tube" Theo Biol Med Model 2008; 5: 15.

Papaioannou et al. "The systolic volume balance method for the noninvasive estimation of cardiac output based on pressure wave analysis." Am. J. Physiol. Heart Circ. Physiol., 302: 2012, H2064-H2073.

Silva, Jennifer MD; "Smartphone-enabled ECG devices effective at detecting arrhythmias in children", Cardiology Today Jun. 10, 2014.

Solosenka et al., "Automatic premature ventricular contraction detection in photoplethysmographic signals" Biomedical Circuits and Systems Conference (BioCAS), 2014 IEEE.

Vardoulis et al. "*On the estimation of total arterial compliance from aortic pulse wave velocity*", Ann. Biomed. Eng., 2012; 40: 2619-2626.

Westerhof et al. "Cardiac muscle mechanics" in "Snapshots of hemodynamics", $2^{nd}$ ed., New York: Springer; 2010; (202pgs); 4-192.

* cited by examiner

PERSONAL HAND-HELD MONITOR TO PRODUCE A THEORETICAL CURVE BASED ON PPG SIGNALS AT DIASTOLE AND SYSTOLE, MEASURED PRESSURE DATA AT DIASTOLE AND SYSTOLE, AND TIMES OF DIASTOLE AND SYSTOLE

This application is a National Stage Application of International Patent Application Serial No. PCT/EP2017/053441, filed Feb. 15, 2017, which claims the benefit of Great Britain Patent Application Serial No. 1602875.5, filed Feb. 18, 2016, the disclosures of both of which are hereby incorporated by reference as if set forth in their entirety herein.

1. FIELD OF THE INVENTION

The present invention relates to a personal hand-held monitor for deriving one or more measurements of a parameter related to the health of a subject from data collected by that personal hand-held monitor.

2. ABBREVIATIONS

In this application, the following abbreviations are used: PHHM—Personal Hand-Held Monitor; SAD—Signal Acquisition Device; PHHCD—Personal Hand-Held Computing Device; BP—Blood Pressure; DBP—Diastolic Blood Pressure; SBP—Systolic Blood Pressure; PPG—photoplethysmograph or photoplethysmogram; ECG—Electrocardiogram; SCG—seismocardiogram; PEP—Pre-Ejection Period.

A PHHM as used herein includes a SAD and a PHHCD. In general, the SAD is adapted solely to acquire and condition signals which are then processed by a processor in the PHHCD or with which the PHHCD communicates to derive the one or more parameters related to the health of the subject.

The term "subject" refers to the person whose personal health data is being collected. The term "user" refers to the person who is using a PHHM to collect personal health data. The user may be the subject or may be another person, such as a health care professional, family member or friend who uses or assists the subject to use the PHHM to collect the subject's personal health data.

3. BACKGROUND TO THE INVENTION

WO 2013/001265, in the name of Leman Micro Devices SA, discloses a PHHM comprising a SAD for acquiring signals which can be used to derive a measurement of a parameter related to the health of the subject, the SAD being integrated with a PHHCD. WO 2013/001265 also discloses a SAD adapted to be integrated with a PHHCD to produce a PHHM as described therein. WO 2013/001265 in its "Background to the Invention" section provides a review of prior art of which the Applicant was aware at the time. WO 2013/001265 includes disclosures relating to the measurement of a subject's BP by pressing the SAD against one side only of a body part or by pressing one side only of a body part against the SAD. The SAD may comprise a pad filled with a fluid in which is located a sensor for determining the pressure in the fluid.

WO 2014/125431, also in the name of Leman Micro Devices SA, discloses a PHHM which comprises a SAD for acquiring signals which can be used to derive a measurement of a subject's BP, the SAD being integrated with a PHHCD. The SAD comprises a blood flow occlusion means adapted to be pressed against one side only of a body part or to have one side only of a body part pressed against it, a means for measuring the pressure applied by or to the body part, and a means for detecting the flow of blood through the body part in contact with the blood flow occlusion means. The blood flow occlusion means comprises at least part of an external surface of the PHHM and the pressure is sensed by means of a flexible and essentially incompressible gel in which is immersed a pressure sensor. The pressure sensor is adapted to provide electrical signals to the processor of the PHHCD. The surface of the blood flow occlusion means may be saddle-shaped.

International Patent Application No. PCT/EP2015/079888, also in the name of Leman Micro Devices SA, discloses a SAD for acquiring signals which can be used to derive a measurement of a subject's BP and, optionally, one or more other vital signs, the SAD comprising: a housing adapted to be located on a PHHCD or a hand-held component of a computing system; a flexible and essentially incompressible gel located in the housing such that, when the housing is located on the PHHCD or the hand-held component, an open surface of the gel is available to be pressed against a body part of the subject or to have a body part of the subject pressed against it; a pressure sensor embedded in the flexible and essentially incompressible gel, which sensor is adapted to provide an electrical signal indicative of the pressure applied to or by the open surface; a means for detecting the flow of blood in the body part of the subject when pressure is applied to or by the open surface, the blood flow detecting means being located on the housing or in the flexible and essentially incompressible gel; and means for receiving electrical signals from the pressure sensor and the blood flow detecting means and for transmitting electrical signals indicative of the pressure and blood flow to the processor of the PHHCD or the computing system. This application also discloses PHHMs containing the SAD and methods for collecting and processing data to derive a measurement of a parameter related to the health of the subject, in particular, the subject's BP.

WO 2013/001265, WO 2014/125431 and International Patent Application No. PCT/EP2015/079888 (collectively "the Leman applications") disclose PHHMs which, depending on which features are included in the SAD or the PHHCD, can generate simultaneously several accurate data streams related to the measurement of parameters related to the health of the subject, including BP (SBP and DBP), a PPG, the pressure applied to the artery from which the PPG is found and an ECG. They also show how it is possible to process the data streams to provide measurements related to the health of the subject.

The above-referenced Leman patent applications disclose a number of related inventions which can be used separately or together to make available a PHHM which can provide measurements of one or more parameters related to a subject's health. The inventions disclosed in the above-referenced Leman patent applications are referred to collectively as "the prior Leman inventions".

The prior Leman inventions can provide powerful solutions to the problem of making widely-available a low cost PHHM which can make measurements of parameters related to a subject's health. However, there are still areas where it is possible to make improvements. In particular, some people find it difficult to operate PHHMs according to the prior Leman inventions, the PHHMs according to the prior Leman inventions would benefit from greater accuracy and adaptations that extend the range of health-related parameters which can be measured by the PHHMs according to the prior Leman inventions can be further developed.

4. THE PRESENT INVENTION

The present invention addresses certain areas of the prior Leman inventions where improvement can be made, whilst maintaining the special properties of the prior Leman inventions that allow a SAD to be small and cheap enough to be incorporated into a smartphone to provide a PHHM which can achieve medical accuracy and be easy to use.

It is important to recognise that much of the value of the prior Leman inventions lies in their completeness and coherence. The benefits of the prior Leman inventions arise from the fact that together they address all of the challenges of a PHHM that allow it to be ubiquitous. The SAD defined by the prior Leman inventions can be incorporated into many PHHCDs and in particular into many smartphones and the evidence of other innovations in smartphones, such as cameras or navigation, is that, once these appear, they are adopted for every smartphone. By offering many measurements in a single PHHM, the cost and inconvenience of incorporating an SAD into a smartphone is amortised across all of those measurements. By including within the prior Leman inventions novel ways of manufacturing and calibrating the PHHM, the cost is reduced. Together, these result in a package that is attractive to smartphone manufacturers and therefore will result in wide adoption that allows the costs to be driven down and the medical benefits to be widely distributed.

It is not essential that every one of the aspects of the present invention referred to below is incorporated into every embodiment of a PHHM but preferably all or most of them are incorporated to maximise the value of the PHHM. It follows that the aspects described here should be seen as aspects of a single invention, although they are the subject of several independent claims, and the various aspects can be used in any or all possible combinations.

5. DESCRIPTION OF THE DRAWINGS

The various aspects of the present invention as described below are illustrated, by way of non-limiting example only, with reference to the accompanying drawings, in which.

First Aspect—Enhancement of Beat Data

Figure 1:
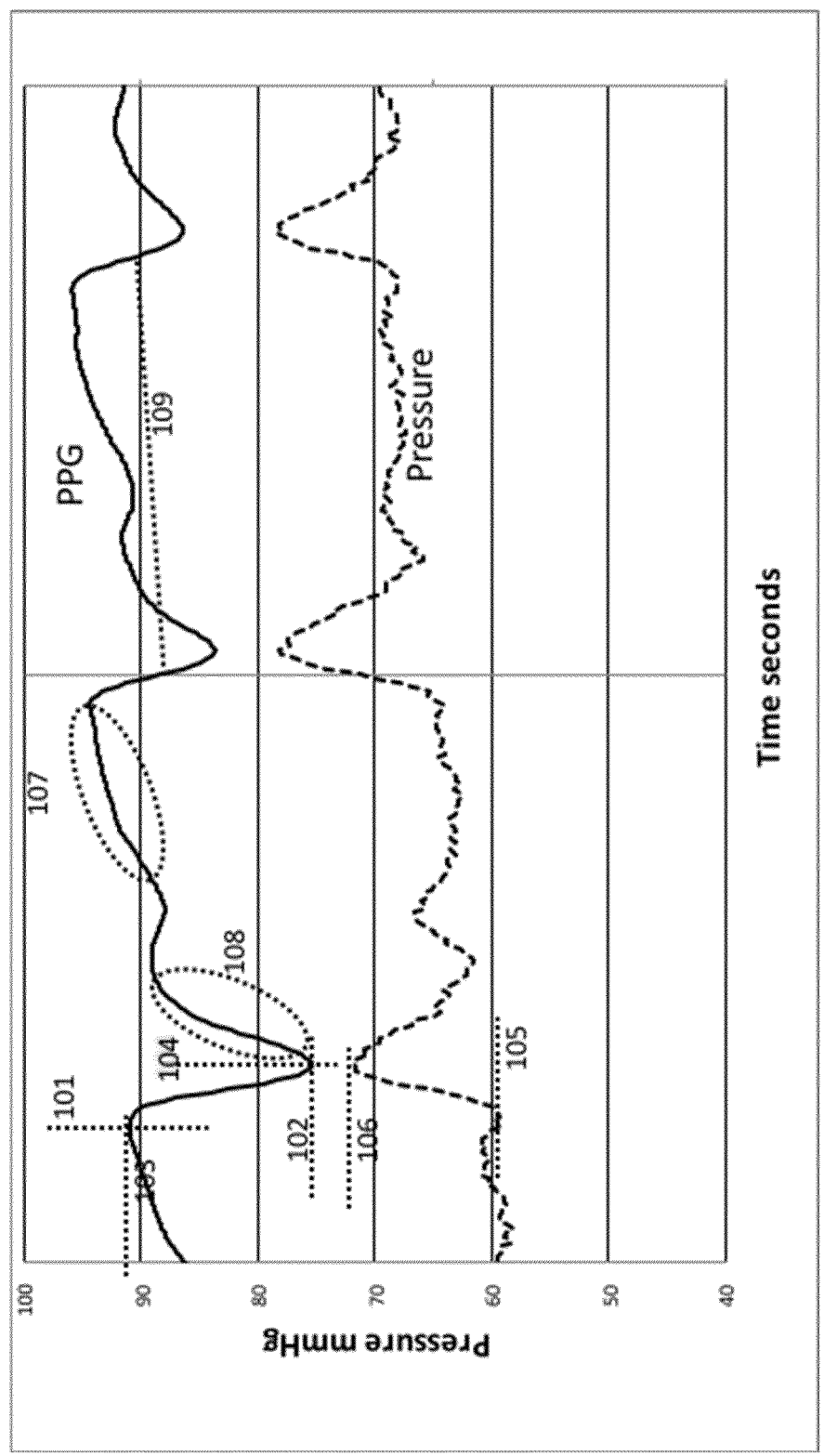
FIG. 1 shows typical recorded data and the regions that are analysed.

In a first aspect of the present invention, the processor of a PHHM comprising a SAD which includes an optical sensor and a pressure sensor, as disclosed in any of the above-referenced Leman applications, is adapted to analyse the measured optical and pressure data which are obtainable from applying the PHHM to the body part or the body part to the PHHM, preferably as described in the fifth aspect below, so that each beat of the heart is characterised by at least one of the features or any combination of two or more of the features illustrated in FIG. 1, wherein the solid line is a recorded infra-red optical signal, the coarse dotted line is the corresponding recorded pressure signal and the fine dotted lines mark the values that are found for each of the features, designated as follows:

TD 101 and TS 104, the times of diastole and systole;
PD 105 and PS 106 the measured pressure at TD and TS;
PPD 103 and PPS 102, the measured PPG signal at TD and TS;
ACD, the high frequency component of the optical signal in region 107 of the curve, being the region before TD;
SHAPED, a measure of the curvature of the plot of the optical signal in region 107 of the curve, being the region before TD;
SHAPES, a measure of the curvature of the plot of the optical signal in region 108 of the curve, being the region after TS;
DUTYCYCLE, the fraction of the values of the optical signal that lies above a straight line 109 constructed from the half height of the falling edge of one PPG trough to the half height of the falling edge of the next PPG trough.

It is useful to measure ACD because this exploits the fluctuations in the optical signal which may result from instability of the arterial wall and/or turbulence in the blood flow.

Preferably, the optical signal is an infra-red signal, as explained in the Leman applications.

The PPG signal arises because the artery expands on each pulse. The expansion causes a change of cross-sectional area and therefore a change in the volume of blood within the field of view of the optical system. This gives rise to a change in PPG signal given by (PPS-PPD), described in detail in the Leman applications and referred to as deltaPPG. The difference in measured pressure between systole and diastole is given by (PS−PD), referred to as deltaP, and also arises because the artery expands.

The pressure signal suffers from measurement errors, caused primarily by the muscular behaviour of the body part pressed against the pressure sensor, which causes deltaP to be more noisy than deltaPPG. To a reasonable approximation, deltaPPG is proportional to the underlying or noise-free deltaP. deltaPPG may therefore be used to find an independent and less noisy estimate of delta P. The processor of the PHHM is adapted to provide three pressure values for each pulse: PD, PS and q, where q is an estimate of (PS−PD) from scaling deltaPPG. PD and PS may be transformed into PM, where PM=(PD+PS)/2, and L, where L=(PS−PD). This transformation is valuable for two reasons. The first is that PM is a useful analysis parameter because it varies more smoothly with pressure than PD (which has a rapid change at DBP) or PS (which has a rapid change at SBP). The second is that the accuracy of L may be enhanced by combining the measured (PS−PD) value with the value q.

Figure 2:
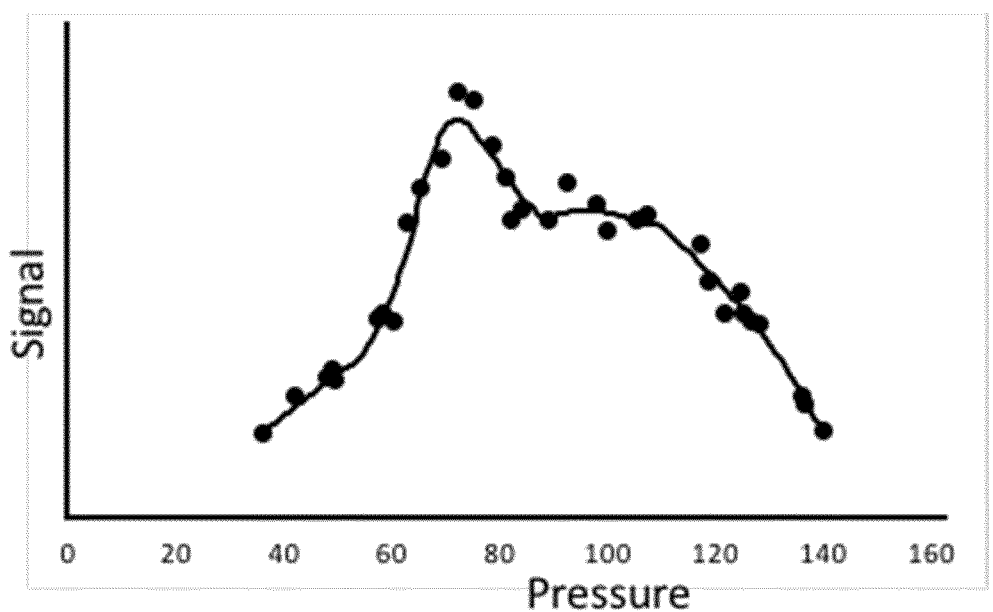
FIG. 2 illustrates use of Loess interpolation.

Further, it has been found, using the inventions described in the Leman applications, that PD and PS do not change monotonically with pulse number (and hence time). WO 2013/001265 states (page 23 line 4): Unlike conventional sphygmomanometry, flow may be detected at a range of pressures in any order and the data fitted to a known mathematical equation. Preferably, the processor is adapted to accept data in any order by interpolating the measured data or parameters derived from it onto a regular grid. Preferably, the processor is adapted to employ a non-parametric regression algorithm, such as Loess regression (see, for example, http://www.statisticshowto.com/lowess-smoothing/), for the interpolation. It is convenient to map the measured data or parameters derived from the measured data against PM and to interpolate typically of the order of 200 points over the range of measured pressures. Such plots, illustrated by FIG. 2, will be referred to as "Loess plots" although it is apparent to a person skilled in the art that other regression/interpolation schemes can be used, including simply analysing the measured data without the benefit of regression or interpolation.

Second Aspect—Extraction of Estimates of DBP and SBP

Extracting DBP and SBP from Loess plots is a special case of finding the pressure waveform in that it only seeks two points on that waveform—its minimum (DBP) and its maximum (SBP). WO 2014/125431, page 28, lines 6 to 21, teaches that there are two independent methods of finding the pressure waveform. Method 1 exploits the shape of the optical data curve (corresponding to the (PPD-PPS) data); method 2 exploits the timing of events when the pressure in the artery exceeds or falls below the pressure applied by the subject.

Preferably, the processor of the PHHM is adapted to conduct several analyses of the measured data, using both methods separately or in combination. PPD, PPS, ACD, ACS, SHAPED, SHAPES and DUTYCYCLE (and combinations thereof) may all be used as the data that are plotted against PD, PS or PM for further analysis and the plot may be either the measured data or its Loess interpolation. Preferably, the processor is adapted to conduct six such analyses. Preferably, the processor is adapted to extract one or more of SBP, DBP and (SBP-DBP) from the analyses.

| Plot used | Feature(s) found | Loess? | Indicates | Method |
|---|---|---|---|---|
| 1 ACD vs PD | Min second derivative | Y | DBP | 1 |
| ACD vs PS | Max second derivative | | SBP | |
| 2 PPD-PPS vs PM | Max first derivative | Y | DBP | 1 |
| PPD-PPS vs PM | Min first derivative | | SBP | |
| 3 PPD-PPS vs PM | Discontinuity (defined below) | N | DBP | 1 |
| PPD-PPS vs PM | | | SBP | |
| 4 DUTYCYCLE vs PM | Min second derivative | Y | DBP | 2 |
| | Max second derivative | | SBP | |
| 5 SHAPED vs PD | Min second derivative | Y | DBP | 1 & 2 |
| SHAPES vs PS | Max second derivative | | SBP | |
| 6 PPD vs PD, | Pressure between | N | SBP - | 1 |
| PPS vs PS | equivalent points | | DBP | |

Figure 3:
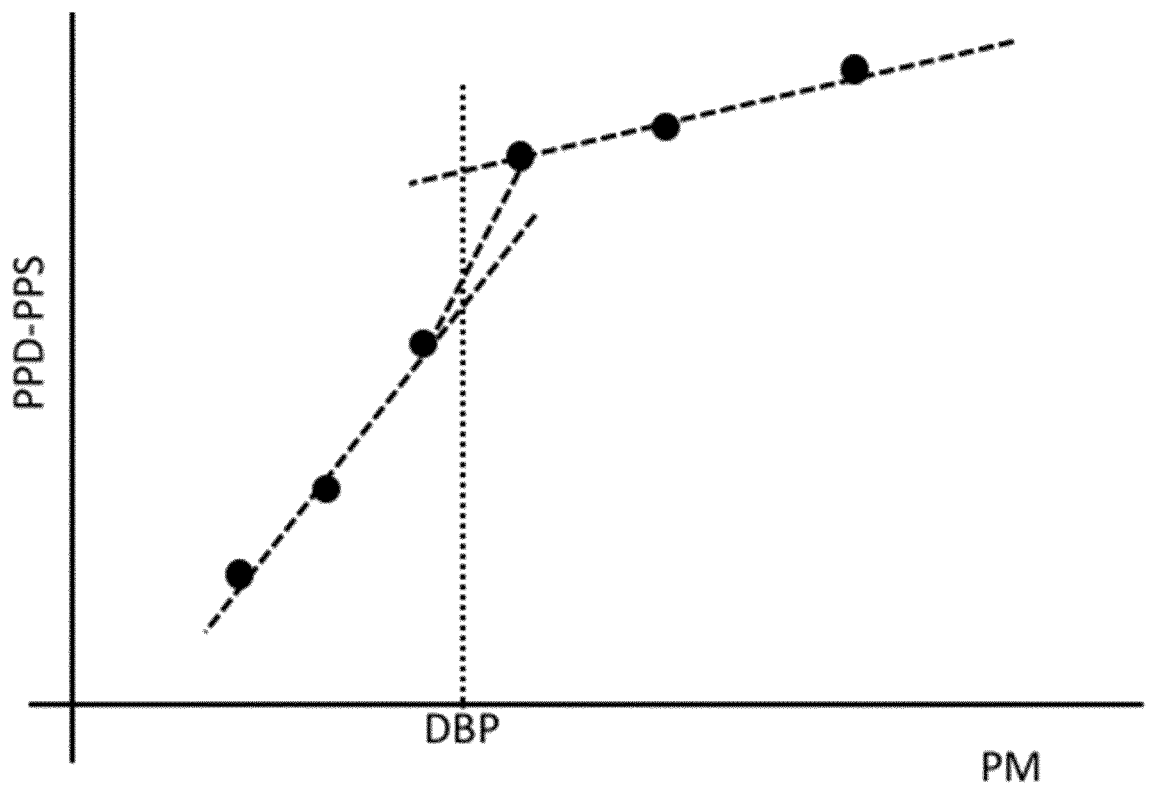
FIG. 3 shows detection of a discontinuity.

The feature referred to as Discontinuity is found by analysing the individual beats without interpolation. This process is illustrated in FIG. 3, where the discontinuity at DBP can be clearly seen.

Each of the analyses involves fitting data to laws or curves. Preferably, the precision of the fit is calculated by finding how closely the measured data match the anticipated curve and the calculated precision may be used as an indicator of the quality of the analysis.

Preferably, the analysis with the best precision is used to indicate SBP and DBP.

Third Aspect—Combination of Estimates

WO 2013/001265 and WO 2014/125431 teach that it is possible to improve the accuracy of an estimate of BP by combining estimates made using different techniques. Pages 16 and 43 respectively present some combinations of techniques.

The first and second aspects of the present invention show that it is possible to make several estimates of SBP and DBP and to calculate an indication of the precision of each. Preferably, the processor of the PHHM is adapted to combine them to find the most accurate estimate of each of SBP and DBP.

Preferably, the combination is found by calculating a weighted average of the separate estimates, where the weights are determined by:
  empirical analysis of the theoretical contribution that each can make to the result; and
  the indicated precision of each.

Preferably, the weighted mean takes the form:

$$SBP = \Sigma_{m=1\ to\ n}(SBPm*Wm*Qm)/\Sigma_{m=1\ to\ n}(Wm*Qm)$$

where:
  SBPm is the mth estimate of SBP;
  Wm is the weight attributed to that mth estimate, representing its theoretical contribution; and
  Qm is a measure of the precision of the mth estimate
and similarly for DBP.

It is apparent that if, for any reason, the algorithm is unable to extract a sensible value of the mth estimate, it may set the weight Wm to zero. In the event that all weights are set to zero, the algorithm returns a message that it is unable to analyse the data.

The empirical analysis of the theoretical contribution that each can make needs to be based on the results of many independent measurements of SBP and DBP and has to take account of both the intrinsic accuracy of each analysis and its correlation with the others. Thus, estimates of SBP and DBP derived from two analyses that have errors that are closely correlated are likely to be similar so there is little to be gained from taking both of them, whereas two analyses with errors that are poorly correlated can be greatly improved by taking their weighted average. The optimal weighting may be found analytically but, preferably, machine learning is used to find the optimum.

Preferably, the processor of the PHHM is adapted to find the quality of the resulting weighted mean by calculating the discord between the separate estimates. Preferably, the discord is defined as the standard deviation of the separate estimates of SBP and DBP.

Fourth Aspect—Correction for Finger Position

Figure 4:
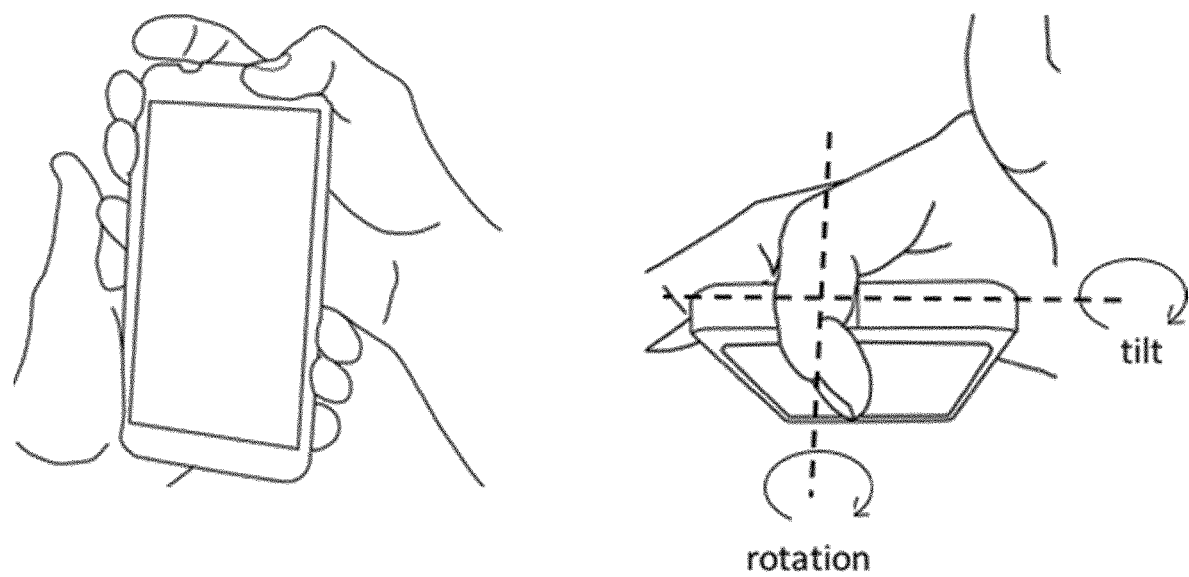
FIG. 4 shows how a PHHM comprising a SAD incorporated into a smartphone can be used to create a trigger action, holding the smartphone in the left hand and placing the right index finger on the SAD.

The pressure experienced by the artery is affected by its location with respect to the pressure sensor of the PPHM. There are two principal effects:
  the artery may be displaced laterally, for example because the finger is rotated about its long axis. This will have the effect of causing the pressure at the artery to be lower than the pressure at the pressure sensor and so will cause the measured pressure at which occlusion occurs to be high: this effect may be referred to as "rotation" and is illustrated in FIG. 4; and the finger may be rotated about and parallel to the face of the PHHCD on which the SAD is mounted or it may be displaced so that the curve of the bone in the second phalanx is pressing on the PPHM. Both of these will cause the measured pressure at which occlusion occurs to be low: this effect may be referred to as "tilt", and is also illustrated in FIG. 4.

Preferably, the processor of the PHHM is adapted to make estimates of the degree of rotation and/or tilt in any measurement of SBP and DBP. PCT/EP2015/079888 teaches that it is possible to estimate the magnitude of rotation by several different means. Preferably, rotation is estimated from the data that have already been measured, as set out in paragraphs 0143 to 0145. Preferably, the processor of the PHHM is adapted to make one or more such estimate of rotation and/or similarly make one or more estimate of tilt. Such estimates of rotation and tilt are referred to as "corrections".

Preferably, the processor is adapted to establish empirical relationships between the values of one or more corrections and the differences between the best estimates of SBP and DBP found according to the third aspect of the present invention and the true values of SBP and DBP respectively. Preferably, the processor of the PPHM is adapted to use these empirical relationships to correct the estimates of SBP and DBP that are derived according to the third aspect to give more accurate estimates of SBP and DBP. Preferably, the empirical relationships are derived using machine learning from a large body of measured results.

Fifth Aspect—Applying to the Body Part

According to a fifth aspect of the present invention, there is provided a PHHM of the type disclosed in the Leman applications which comprises a PHHCD in which is mounted a SAD wherein the SAD is mounted on the PHHCD to allow easy and accurate operation by the user. In the previous Leman applications, it is taught that the user should press a body part of the subject against the SAD or press the SAD against the body part of the subject. Preferably, according to this aspect of the invention, the body part is the index finger and the device is configured as described below so that the user can create the pressure by using the device like the trigger of a gun.

This is a more natural action than pressing the side of the finger downwards and ensures that there is a cushion of soft tissue around the artery to give a more constant pressure field, both of which lead to more accurate and easier measurements.

This is illustrated in FIG. 4. The SAD is incorporated into the top of a smartphone, which is held in the left hand. The index finger of the right hand is rested on the SAD, with the centre of the middle phalanx pressing against the SAD. Preferably, the PHHM is adapted to provide audible or visual instructions to which the user may respond to increase or reduce the pressure, as described in WO 2013/001265, page 23, line 6, by adjusting how hard the finger is pressed against the device.

Figure 5:
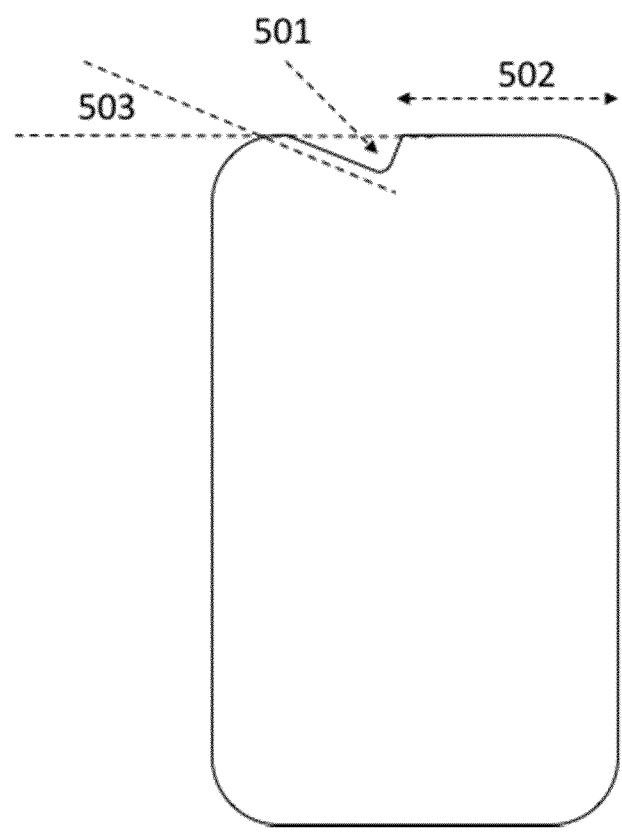
FIG. 5 shows geometrical factors affecting the position of the hand.

FIG. 5 shows the geometrical factors that must be adjusted for this to be effected. The SAD is shown as a notch 501. The distance 502 of the SAD from the edge of the PHHCD on which the ball of the thumb rests and the slope 503 of the SAD must be chosen to suit the average size of hands and the typical location of the artery. If this is done correctly, the subject pulls the finger towards the ball of the thumb and creates pressure on the region of the finger containing the artery.

Sixth Aspect—Detection of Arrhythmia

The present invention provides a PHHM of the type disclosed in the Leman applications which has been adapted to process data streams from sensors in the SAD so that other parameters related to the health of the subject can be derived from those data streams. The PHHMs of the present invention may use sensors that are typically found in a PHHCD or may use sensors specifically incorporated into the SAD. The processor of the PHHM is adapted to process data streams from these sensors to provide measurements of parameter(s) related to the health of the subject. The processor of the PHHM of the present invention is adapted to integrate the data streams from the various sensors to make reliable and effective measurements of parameter(s) related to the health of the subject. The PHHM of the present invention can draw on the integration of the SAD with the PHHCD to exploit the simultaneous data streams from the SAD and from the PHHCD within the PHHM.

The PHHM of the present invention preferably is adapted to instruct the user to adjust the pressure applied to the SAD, as disclosed in the Leman applications.

Figure 6:
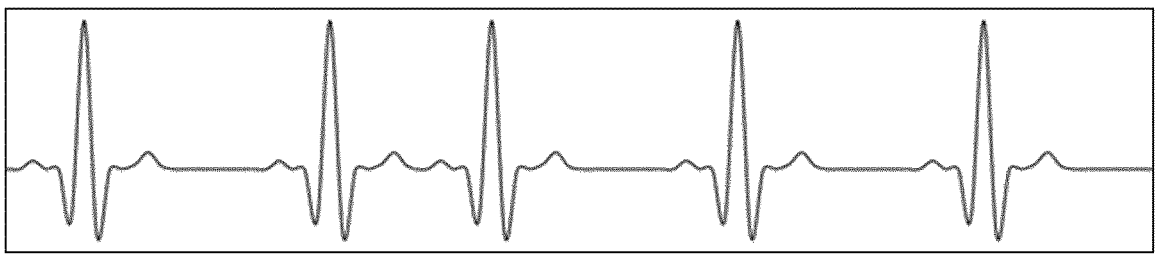
FIG. 6 shows an ECG trace with an arrhythmia.

An ECG signal from a PHHM may be used to detect arrhythmia (see, for example, "*Smartphone-enabled ECG devices effective at detecting arrhythmias in children*", Cardiology Today Jun. 10, 2014). The change in rhythm is detected solely from the timing of the heart beat. This is illustrated in FIG. 6, where the interval between the second and third beats is shorter than normal.

According to a sixth aspect of the present invention, there is provided a PHHM of the type disclosed in the Leman applications which includes sensors from which a PPG can be derived and wherein the processor is adapted to process signals received from the PPG sensors to provide an indication as to whether the subject has an arrhythmia.

Preferably, the sensors are electrical sensors from which an ECG can be derived and sensors from which a PPG can be derived and wherein the processor is adapted to process signals received from the ECG sensors and the PPG sensors to provide an indication as to whether the subject has an arrhythmia.

Figure 7:
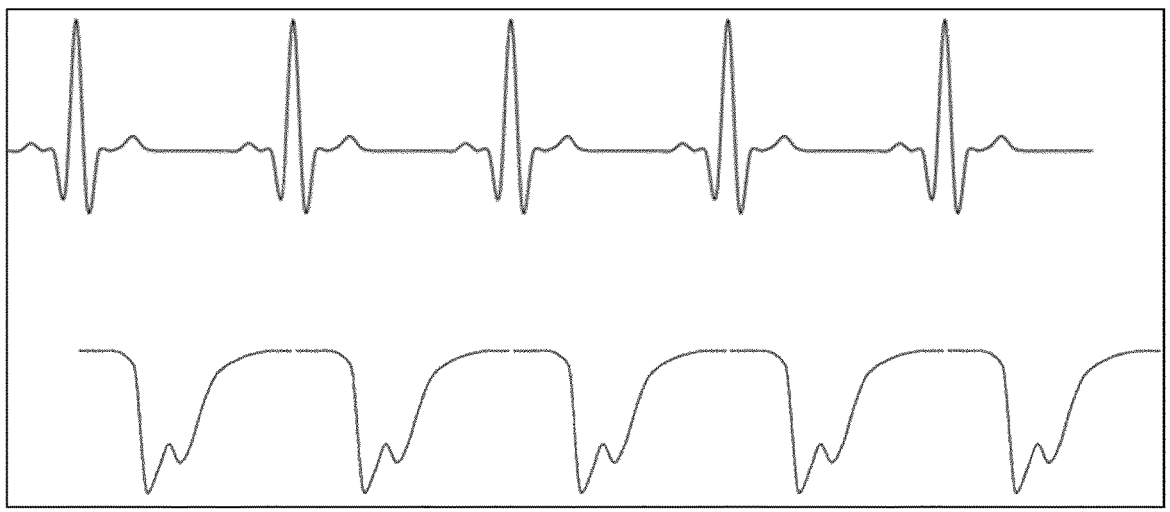
FIG. 7 shows simultaneous ECG and PPG traces.
Figure 8:
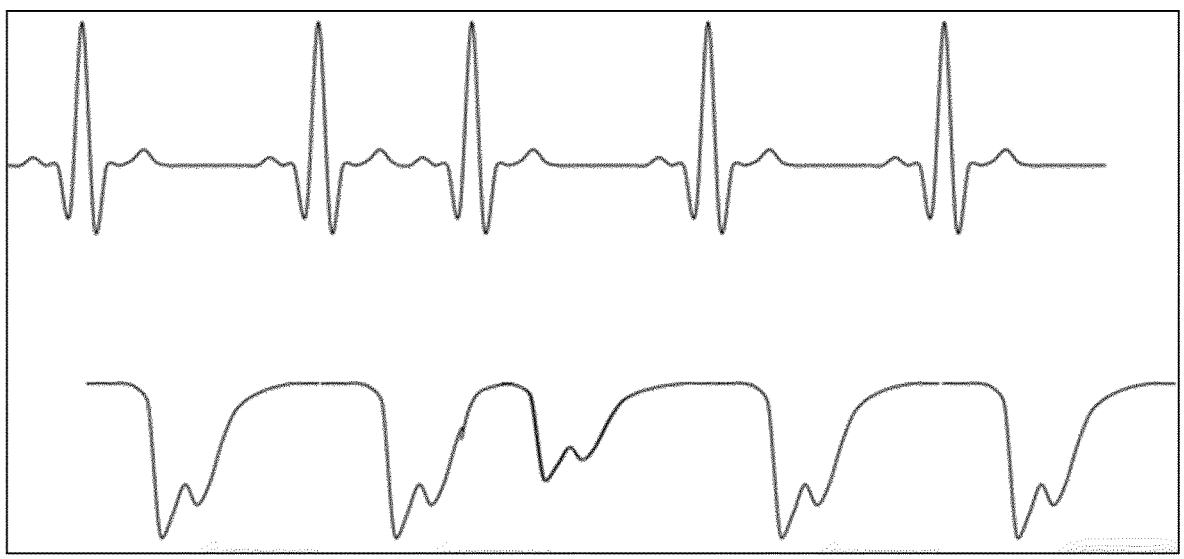
FIG. 8 shows simultaneous ECG and PPG traces with an arrhythmia.

Solosenka et al., "*Automatic premature ventricular contraction detection in photoplethysmographic signals*" Biomedical Circuits and Systems Conference (BioCAS), 2014 IEEE, show how a premature beat causes the volume of blood pumped by that beat to be reduced and a missed beat causes the volume of blood pumped on the next beat to be increased. This is illustrated in FIGS. 7 and 8. In FIG. 7, the upper trace is a representation of the ECG and the lower trace is a representation of the PPG (inverted because that is how it is measured). In FIG. 7, there is no arrhythmia. FIG. 8 shows a premature beat and the consequent effect on the PPG signal.

Arrhythmias may be more reliably detected and classified using the PHHM of the present invention by identifying both the error in timing, using either the ECG sensors or the PPG sensors, and the consequential effect on blood volume, which can be determined from the signals from the PPG sensors. The PHHM is preferably adapted to provide audible or visual instructions to the user to maximize and regulate the PPG signal by adjusting the pressure applied to or by the SAD. The adaptation of the PHHM to use a combination of ECG and PPG signals, with the ability to measure and control the pressure applied to the artery, allows more reliable detection and classification of arrhythmias.

Seventh Aspect—Estimation of Arterial Stiffness

Arterial stiffness is a valuable diagnostic of cardiovascular health.

WO 2013/001265 teaches that the mechanical response of the heart to the natural electrical signals which trigger the beating of the heart may be detected using an acoustic sensor, such as the microphone of a smartphone, in a PHHM. Another sensor that is routinely included in smartphones is an accelerometer.

According to a seventh aspect of the present invention, there is provided a PHHM of the type disclosed in the Leman applications which includes ECG sensors and an accelerometer, wherein the processor is adapted to detect the mechanical response of the heart to the natural electrical signals which trigger the beating of the heart by holding the PHHM against the chest and processing signals from the ECG sensors and the accelerometer. The accelerometer signal so derived is conventionally referred to as a Seismo-CardioGram ("SCG").

Figure 9:
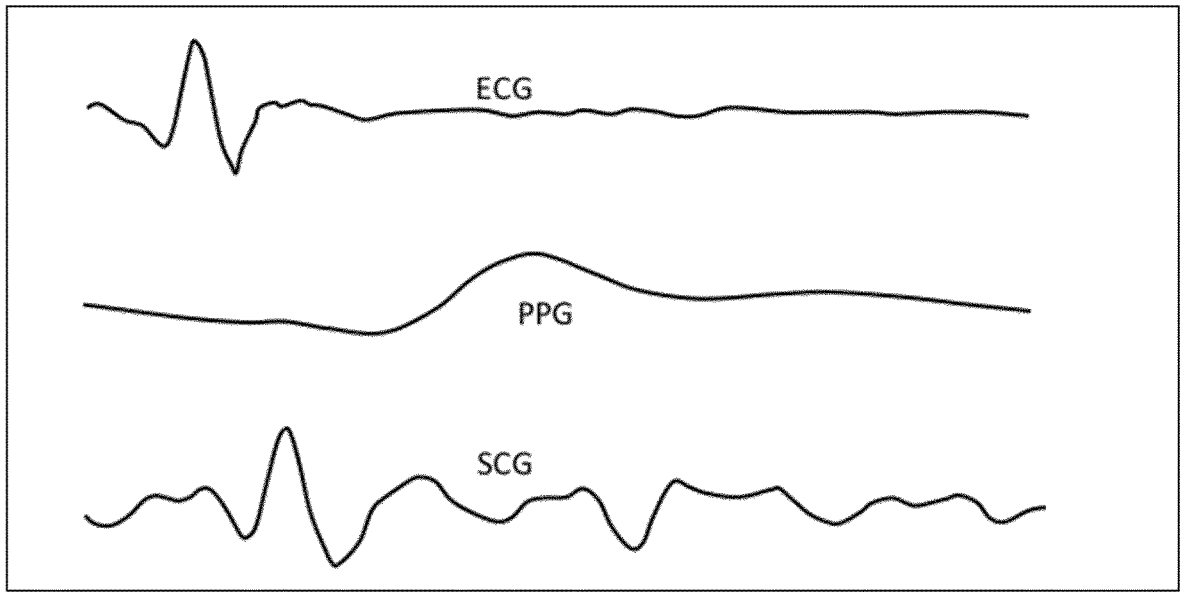
FIG. 9 shows measured simultaneous ECG, PPG and BCG signals.

Typical results of measuring simultaneously the ECG, PPG and SCG signals are shown in FIG. 9, where the SCG signal is the component aligned with the long axis of the smartphone and the base of the smartphone is held against the sternum. It will be apparent to a person skilled in the art that the smartphone may be held against other body parts that vibrate when the heart pumps and that other components or combinations of the components may be measured.

Preferably, the data shown in FIG. 9 are obtained by processing over several beats, advantageously over 10 or more beats. Preferably, the signal processing scheme involves:
  synchronizing the data from each beat against the ECG QRS complex;
  normalizing the measured data for each beat; and
  summing over several beats, advantageously over 10 or more beats, to improve the signal/noise ratio.

A period of recording of no more than one minute is sufficient to gather the data as shown.

Figure 10:
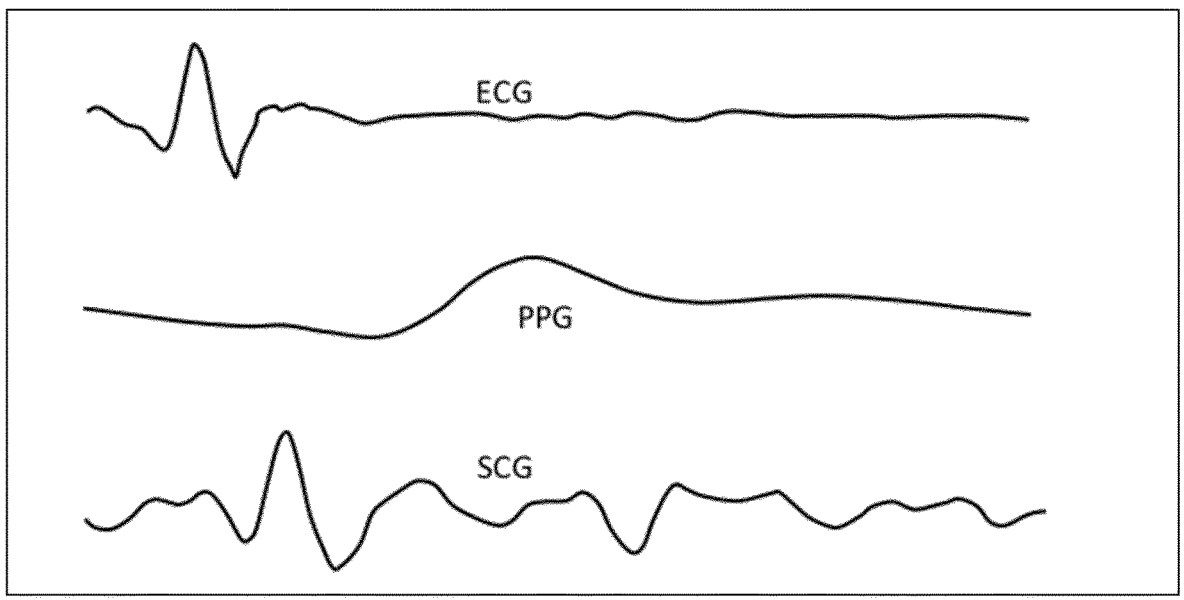
FIG. 10 shows the data of FIG. 8 with PEP and PTT marked.

FIG. 10 shows the same data as FIG. 9 but with two features designated. The interval between the peak in the ECG and the first peak in the SCG is the Pre-Ejection Period (PEP), which is the interval between the triggering of the heart and the response of the muscle. The interval between the end of the PEP and peak in the PPG is the Pulse Transit Time (PTT), which is the time taken for the pressure wave to reach the peripheral artery at which the PPG is measured.

Preferably, the processor is adapted to find the Average Pulse Wave Velocity (APWV) by dividing an estimate of the distance from the heart to the peripheral artery by PTT. Such an estimate may be made by asking the user to enter a scale parameter such as the subject's height. Preferably, the processor is adapted to relate APWV to average arterial stiffness by the Moens-Korteweg equation, as described in for example Painter "*The velocity of the arterial pulse wave: a viscous fluid shock wave in an elastic tube*" Theo Biol Med Model 2008; 5: 15.

Alternatively, the processor is adapted to find PTT using a camera in the smartphone that views the subject (a so-called "selfie" camera) to detect a change in colour of the skin when the pulse reaches the face and finding the time between this and the time of the peak in the PPG. In this case, the relevant length scale is the distance from the carotid artery to the peripheral artery.

Preferably, the processor of the PHHM is also adapted to find a local estimate of arterial stiffness. WO 2014/125431, page 37, line 24 et seq. teaches that it is possible to use the PPG signal to find the relationship between the luminal area of an artery and the pressure in the artery, which is referred to as the Arterial Optical/Pressure Curve (AOPC). This relationship may be approximated by a power law. The exponent of the power law is a direct measure of the stiffness of the artery. Typically, the AOPC has an exponent of 0.25 for a stiff artery and 0.45 for a soft artery.

The processor may be adapted to find the exponent of the AOPC directly by either one of two means.

Figure 11:
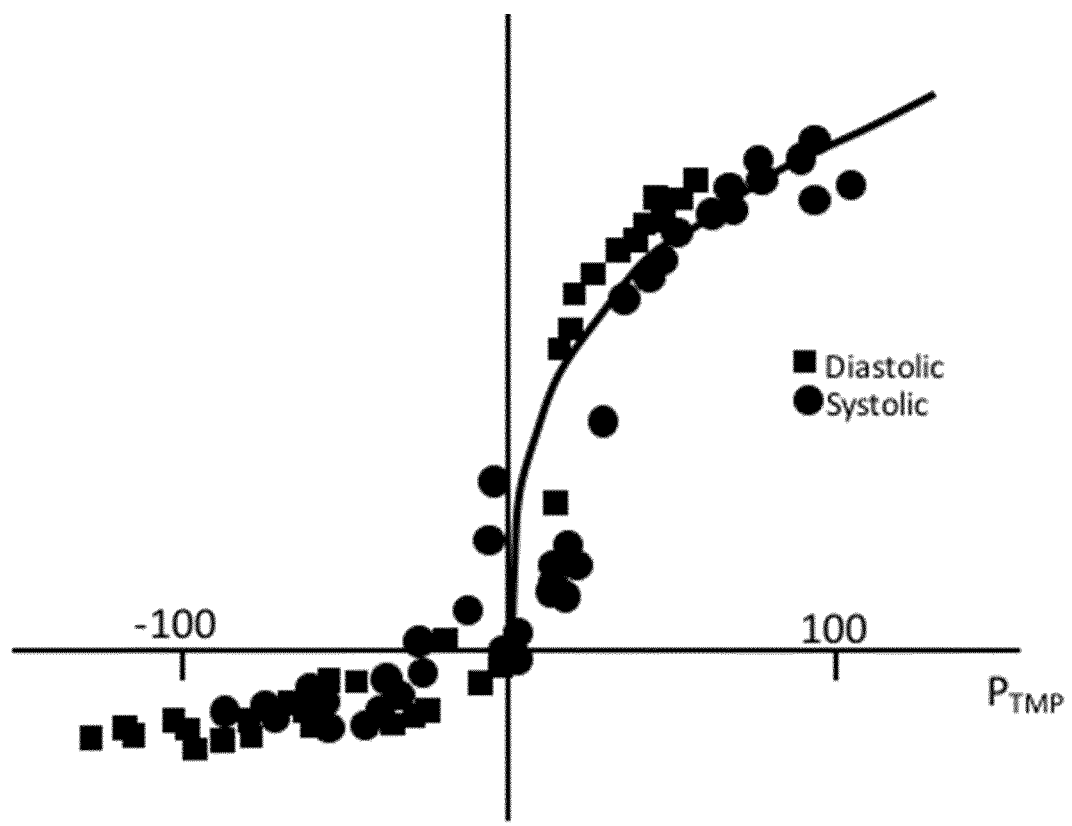
FIG. 11 shows a plot of a PPG signal against trans-mural pressure, at diastole and at systole.

FIG. 11 shows the first means. It is the result of plotting the instantaneous PPG against PTMP, the trans-mural pressure. PTMP is given by (DBP-applied pressure) for the PPG values at diastole and by (SBP-applied pressure) for the PPG values at systole.

Figure 12:
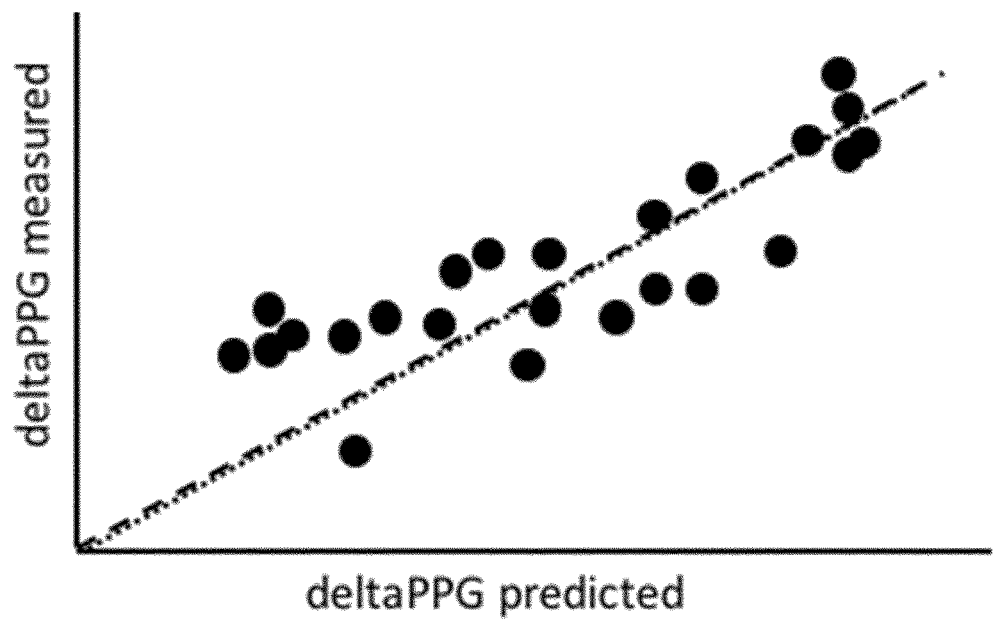
FIG. 12 shows a plot of the measured change in PPG from diastole to systole against its predicted value, where the prediction has been made using an optimised power law.

FIG. 12 shows the second means, which uses the difference between the PPG at diastole and at systole. The vertical axis is the measured difference and the horizontal axis is the predicted difference assuming a power law. The graph is the result of an iterative search to find the exponent for which the points are closest to a straight line through the origin.

Westerhof et al. "*Cardiac muscle mechanics*" in "*Snapshots of hemodynamics*", 2nd ed., New York: Springer; 2010 show that peripheral arteries are smaller, with a larger wall thickness and stiffer than the aorta. The local pulse wave velocity found from this power law should therefore be higher than the average pulse wave velocity. The two together provide more information on the cardiac health of the subject than each alone.

Eighth Aspect—Estimation of Cardiac Output

According to an eighth aspect of the present invention, there is provided a PHHM of the type disclosed in the Leman applications in which the processor is adapted to process signals from ECG and PPG sensors and accelerometers to determine a measure of cardiac output.

From one or more measures of arterial stiffness as described in the seventh aspect of the present invention, it is possible to find an estimate of cardiac output, which is a further diagnostic of cardiovascular health. Vardoulis et al. "*On the estimation of total arterial compliance from aortic pulse wave velocity*", Ann. Biomed. Eng., 2012; 40:2619-2626 show how the Bramwell-Hill equation gives the total arterial compliance. Papaioannou et al. "*The systolic volume balance method for the noninvasive estimation of cardiac output based on pressure wave analysis*." Am. J. Physiol. Heart Circ. Physiol., 302: H2064-H2073, 2012 show how to find cardiac output by balancing the flow from the heart with the volume of blood held in the distended arteries.

Preferably, the processor of the PHHM is adapted to estimate the cardiac output using these estimates of arterial stiffness.

Ninth Aspect—Timing of Cardiac Functions

Figure 13:
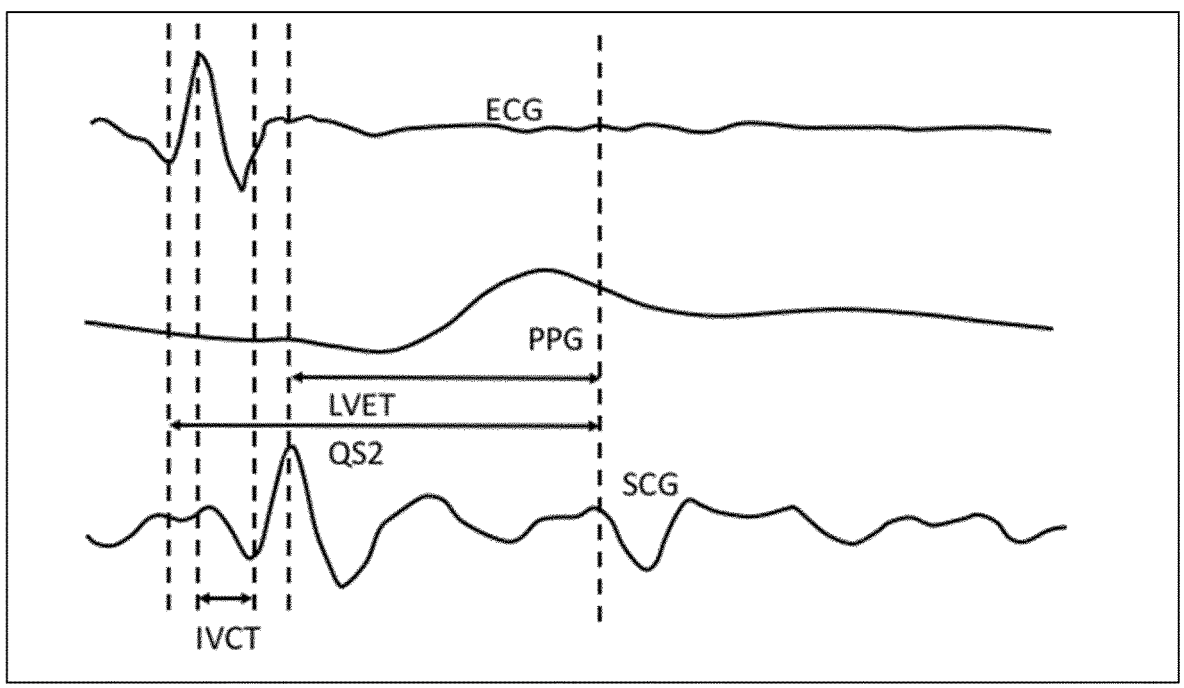
FIG. 13 illustrates some of the valve timings that may be found from the measured data.

The ninth aspect of the present invention is a PHHM according to the Leman applications wherein the processor is adapted to determine the timing of cardiac functions by processing signals caused by vibrations caused by the movements of the heart. FIG. 13 uses the same data as shown in FIGS. 8 and 9 but additional features have been marked. The opening and closing times of the mitral (MO, MC) and aortic (AO, AC) valves are found and may be used to estimate several systolic diagnostic parameters:
LVET—Left ventricular ejection time (AC-AO);
QS2—Electromechanical systole (AC-ECG QRS peak) (=PEP+LVET); and
IVCT—Iso-volumetric contraction time (AO-MC);
From these it is possible to find:
CC—Contractility Coefficient (PEP/LVET).

Two other systolic parameters that may be found are the timing of:
RE=Rapid (Ventricular) Ejection; and
RF=Rapid (Ventricular) Filling.

These systolic parameters are of diagnostic value for heart failure, thyrotoxicosis, aortic insufficiency, aortic stenosis, hypertension, patent ductus arteriosus and cardiac amyloidosis.

There are also several diastolic parameters that may be found including:
LVFT—Left Ventricular Filling Time (period from mitral valve opening—mitral valve closure);
IVRT—Isovolumetric Relaxation Time (AC-MO); and
RVFT—Rapid Ventricular Filling Time (MO-RF)
which can be valuable for the diagnosis of angina, cardiomyopathy and hypertension.

Another valuable parameter is:
MPI—Myocardial Performance Index (IVCT+IVRT)/LVET.
which is independent of heart rate and BP and is of diagnostic value for many diseases including congestive heart failure, dilated cardiomyopathy, cardiac amyloidosis.

It is apparent that the timing of the vibrations caused by the movements of the heart, relative to the timing of the ECG and PPG, are of considerable diagnostic value. Preferably, the processor of the PHHM is adapted to find, display and/or transmit to a remote data processing system these timings.

Tenth Aspect—Estimating the Temperature of the Body Part

The PHHM disclosed by the Leman applications is adapted to measure BP by occluding an artery that is suitably accessible in a body part, preferably the index finger. Regulatory mechanisms in the arterial system can restrict the flow of blood to the fingers if they are too cold. Although small restrictions in blood flow have little effect on the measured BP, it is desirable to take account of the temperature of the finger when assessing the quality of the measurement and, if it is too cold, suppressing the result.

When using a PHHM of the Leman applications, the skin of the body part, typically a finger, is in intimate contact with the essentially incompressible gel in which is immersed a pressure sensor. The pressure sensor is typically of the order of 1 mm from the surface of the gel and its temperature very closely follows that of the skin of the body part. However, the temperature of the skin changes when it is pressed against the PHHM for two reasons:
the PHHM insulates the skin from the cooling effect of the surrounding air so the temperature rises as a result of heat convected into the skin by the blood flow;
the current flowing through the components of the PHHM, dominated by the current through the ASIC and LEDs to cause the LEDs to emit light, heats the gel.

The Leman applications teach that it is possible to measure the temperature of the pressure sensor by measuring its total resistance. The ASIC is adapted to generate these data and the processor of the PHHCD is adapted to use the data to correct the measured pressure. Preferably, the initial temperature of the skin is found by measuring changes of the temperature of the pressure sensor after the skin is applied to the gel, taking account of the rate of heating generated by the current through the LEDs.

Preferably, Newton's Law of Cooling and the law of heat conduction are used to find a parametric equation relating the skin temperature to these measured data. Preferably, the parameters are found by regression to experimental results, either analytically or by means of machine learning.

Eleventh Aspect—Calibration of Thermopile

The PHHM disclosed by the Leman applications can include a temperature sensor that detects infra-red radiation and can be used to measure the body temperature and for other measurements. Conventional infra-red temperature sensors use a thermopile, one set of junctions (the "hot junctions") of which is exposed to incident infra-red radiation and the other set of which (the "cold junctions") is assumed to be at the ambient temperature of the SAD. (There is no requirement that the hot junctions be hotter than the cold junctions; these are just terms conventionally applied to them.) The ambient temperature is itself sensed by another sensor, usually a thermistor. Production tolerances require both the thermopile and the thermistor to be individually calibrated.

The Leman applications disclose a calibration system to calibrate the pressure sensor by exposing it to a range of ambient pressures and temperatures. Preferably, the thermistor is calibrated at the same time by recording its value as a function of temperature.

The calibration of the thermopile requires exposing it to infrared radiation that arises from a surface at a known temperature that is different from the ambient temperature of the SAD. It is well-known (see for example U.S. Pat. No. 4,440,716) that this may be done by adding a heater to the temperature sensor so that the ambient temperature may be changed whilst exposing the hot junctions to a surface with a fixed temperature. The sensitivity of the thermopile to temperature may be found by measuring the change in voltage between the hot and cold junctions as a function of the temperature change caused by the heater, which may itself be measured by the thermistor.

The invention disclosed herein adopts a similar approach but uses the LEDs of the PHHM to cause the heating. Preferably, the heating is for a time short enough that it has a negligible effect on the local temperature of the calibration chamber. Preferably, the calibration chamber is adapted to ensure that the hot junctions are exposed to a black surface that is in temperature equilibrium with the rest of the calibration chamber.

Twelfth Aspect—Monitoring the Calibration of the Pressure Sensor

It is indicated in the Leman applications that it is preferred that the pressure sensor used in the SAD is individually calibrated so as to ensure that it gives an accurate reading. Aging of the essentially incompressible gel and variations in humidity can cause the zero value of the calibration to change, where the zero value is defined to be the signal from the pressure sensor at a fixed ambient pressure. Preferably, this is compensated for by measuring the pressure due to the body part relative to its value immediately before the body part is placed on the pressure sensor. Provided the changes to the zero value are slow compared with the time for a measurement of BP (typically less than one minute), they will have no effect on the estimated BP.

The temperature of the pressure sensor changes during the course of a measurement of BP. The calibration of the temperature sensor is designed to compensate for temperature changes but such calibration might not be perfect. Preferably, the processor of the PHHM is also adapted to measure the value from the pressure sensor immediately after the body part is removed. Preferably, the difference between this value and the value obtained immediately before the body part is placed on the pressure sensor is used to interpolate an approximation to the zero value at any time during the measurement.

Preferably, the PHHM is also adapted to be able to detect and correct changes to the sensitivity of the pressure signal with respect to pressure. Many PHHCDs include a reference pressure sensor that gives an accurate estimate of ambient pressure. The value of the ambient pressure changes with the weather and with altitude. Preferably, the PHHM is adapted to record the ambient pressure from the reference pressure sensor and the pressure measured by the SAD when not applied to a body part and to record both measured pressures frequently. This might be every time that the PHHM is used or it could be done automatically, perhaps once per day.

Preferably, the processor of the PHHM is adapted to correlate the two measured pressures as the ambient conditions change to check that the sensitivity of the pressure sensor in the SAD remains within tolerance. Preferably, the processor of the PHHM is adapted to respond to any such change by correcting the reading of the pressure sensor in the SAD, warning the user of a potential error or suppressing measurements and warning the user that the SAD must be returned to the manufacturer for recalibration, according to the magnitude of the change.

Thirteenth Aspect—Electromagnetic Lever

The third aspect of the PHHM disclosed by PCT/EP2015/079888 teaches that it is possible to use a magnetic actuator to measure the pressure applied to the body part or which the body part applies to the PHHM. This approach has several advantages over the use of a conventional pressure sensor embedded in a flexible gel but it requires a strong magnetic field to achieve the necessary force. It operates by holding the button in a constant position, which does not exploit the ability of a magnetic actuator to move a significant distance, of the order of a millimetre or more for the design presented.

According to the thirteenth aspect of the present invention, the capability of the magnetic actuator to move a much greater distance than is needed to make the measurement is used to operate a lever so that a large movement of the actuator is translated into a small movement of the button but with a greater force.

Figure 14:
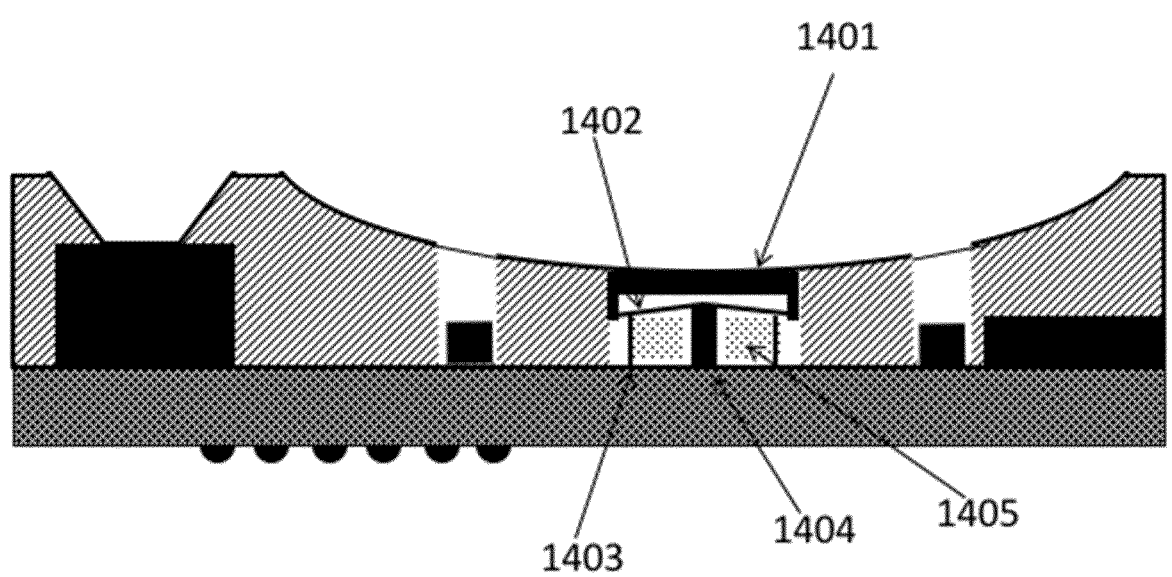
FIG. 14 shows one way of implementing the levers for the magnetic device.

FIG. 14 shows an embodiment of this aspect of the present invention. The button 1401 has attached to it two lever arms 1402. These rest on two fulcrums 1403 and are attached to a rod 1404 of ferromagnetic material. A coil 1405 of conducting wire surrounds the rod 1404. The rod 1404 slides in the coil 1405 and pulls the lever arms down, which causes the button to rise.

Fourteenth Aspect—Improved Identification

PCT/EP2015/079888 teaches that it is possible to identify the user from the data obtained from the SAD. It identifies several features of the data that may be used and teaches that a Bayesian approach may be taken to combine them to give a more accurate estimate of the identity.

One advantage of the Bayesian approach is that it allows further data to be included. According to a fourteenth aspect of the present invention, the parameters defined in the ninth aspect of the present invention may be used in the Baysian estimator to improve the accuracy of the identification.

Fifteenth Aspect—Non-Resting BP

Conventional medical practice uses resting BP as a diagnostic. Resting BP is measured when the patient has been sitting calmly, relaxed with the back supported and feet flat on the floor for 3 minutes. Any deviations from this state can cause significant changes to the BP. An extensive review conducted by the Brazilian Society of Cardiology (Arc Braz Cardiol 85, 2 Jul. 2005, http://dx.doi.org/10.1590/S0066%AD782X20050021000001IV) found a range of 30 mmHg in SBP and 23 mmHg in DBP, depending on the activity being undertaken. There is great interest in devices that make measurements under non-resting conditions, including continuous measurements, but medical practice has great difficulty in interpreting their significance.

Preferably, the PHHM includes instructions for the user to follow the protocol for measuring resting BP. However, it is likely that users will make measurements under other conditions. Preferably, the processor of the PHHM is adapted to invite the user to enter a statement of what the subject was doing at the time of the measurement. Preferably, the PHHM displays a table of possible activities and circumstances, such as walking, eating, standing, optionally with a free-text entry to allow others to be recorded, one of which can be selected by the user.

Preferably, the selection made by the user and any statements entered by the user are transmitted to a remote data processing system together with the data recorded during the measurement for subsequent analysis. Many PHHCDs use data derived from the sensors that they carry to detect each step taken by the subject when walking or running. Other data indicative of the current activities of the subject might be derived from the signals from one or more microphones in the PHHCD, analysis of the vibrations measured by the accelerometers and the signals from any other sensors that are included. Preferably, any or all such data are also transmitted to the remote data processing system.

Preferably, the remote data processing system allows the user to generate a summary of the measurements of BP made under non-resting conditions that may be offered to the subject's medical practitioner.

Preferably, known scientific data, such as the Brazilian data mentioned above, is used by the remote data processing system to estimate the resting BP from the measurements under non-resting conditions and the result returned to the subject. Once this is proven, the processor of the PHHM may be adapted to conduct this analysis locally.

The remote data processing system will build up a large database of the measured BP from many different subjects under many different conditions. Preferably, this database is analysed to find better estimates of the resting BP from estimates made under non-resting conditions. Preferably, the analysis uses regression algorithms and/or machine learning to find better relationships between the reported and/or measured conditions of the measurement and the error in the estimated BPs.

A further opportunity is to identify the relationship between the changes in measured BP caused by measuring under non-resting conditions and health. This allows the changes to be used as a diagnostic tool. Preferably, the analysis of the data by the remote data processing system is also correlated with medical history and diagnosis by other means in order to find information of diagnostic value from the changes.

Preferably the results of this analysis by the remote data processing system are used to interpret continuous measurements of BP.

Sixteenth Aspect—Comparative Results

Preferably, the processor of the PHHM is adapted to display to the user an indication of how the subject's measured values compare with the statistics of the general population. For example, this might take the form of a message "Your pulse is slower than that of 73% of the population" or, if the subject has entered his/her age and sex, it might display a message of the form "Your blood pressure is lower than that of 57% of women of your age".

The statistics on which such messages are based can initially be taken from the published literature but preferably are refined by using the data on measurements made by any PHHMs in use and saved on the remote data processing system.

The invention has been described above by way of illustration only but is not limited to the illustrated embodiments. Rather, the scope of the present invention is as defined in the following claims.

The invention claimed is:

1. A personal hand-held monitor (PHHM) configured to derive one or more measurements of a parameter related to health of a subject from data collected by the PHHM, the PHHM comprising:
   a signal acquisition device (SAD) which includes an optical sensor and a pressure sensor, wherein the optical sensor is a photoplethysmography (PPG) sensor; and
   a processor;
   wherein the processor of the PHHM is configured to analyse measured optical data and measured pressure data which are obtainable from applying the SAD to a body part or applying a body part to the SAD;
   wherein:
   the processor is further configured to derive timing data indicating a time of systole (TS) and a time of diastole (TD) during application of the SAD to the body part or the application of the body part to the SAD; and
   the processor is configured to produce a theoretical curve from which each beat of a heart is characterised based on:
      the photoplethysmography signal at diastole (PPD) and photoplethysmography signal at systole (PPS), where PPD and PPS are the measured PPG sensor signals at TD and TS, respectively,
      the measured pressure data at diastole (PD) and the measured pressure data at systole (PS), where PD and PS are the measured pressure sensor signals at TD and TS respectively, and
      TD and TS;
   wherein the processor of the PHHM is configured to calculate, for each beat, deltaPPG, deltaP and q, wherein:
      deltaPPG=PPS−PPD;
      deltaP=the measured pressure data at systole minus the measured pressure data at diastole; and
      q is an estimate of a pressure at systole minus a pressure at diastole from scaling deltaPPG; and
   wherein the processor of the PHHM is configured to transform PS and PD into PM and L,
   wherein:
      PM=(PS+PD)/2; and
      L=PS−PD.

2. The PHHM of claim 1, wherein the processor of the PHHM is configured to enhance accuracy of L by combining PS−PD with q.

3. The PHHM of claim 2, wherein the processor of the PHHM is configured to accept data in any order by interpolating the measured pressure data, the measured optical data, and/or the timing data, or parameters derived from the measured pressure data, the measured optical data and/or the timing data, onto a regular grid.

4. The PHHM of claim 3, wherein the processor is configured to employ a non-parametric regression algorithm for the interpolating and, optionally, a Loess regression.

5. The PHHM of claim 4, wherein the processor of the PHHM is configured to map the measured pressure data, the measured optical data and/or the timing data or parameters derived from the measured pressure data, the measured optical data and/or the timing data against PM and to interpolate an order of 200 points over a range of measured pressures.

6. The PHHM of claim 1, wherein the parameter is the subject's blood pressure and the processor of the PHHM is configured to conduct a further analysis to extract an estimate of systolic blood pressure (SBP) and diastolic blood pressure (DBP) from the measured pressure data, the measured optical data and/or the timing data, or from processed data as processed from the measured pressure data, the measured optical data and/or the timing data by the processor.

7. The PHHM of claim 6, wherein the processor of the PHHM is configured to conduct at least two analyses of the measured pressure data, the measured optical data and/or the timing data independently and to combine them to find the most accurate estimate of SBP and DBP.

8. The PHHM of claim 7, wherein each analysis involves fitting data to the theoretical curve.

9. The PHHM of claim 1, wherein each beat of the heart is further characterised by TD and a high frequency component of the measured optical signal in a region before TD (ACD).

10. The PHHM of claim 1, wherein each beat of the heart is further characterised by one or more of:
    a measure of a curvature of a plot of the measured optical signal in a region before TD (SHAPED); and
    a measure of a curvature of a plot of the measured optical signal in a region after TS (SHAPES).

11. The PHHM of claim 8, where precision of the fitting is calculated by comparison with an anticipated curve.

* * * * *